US006455318B1

(12) United States Patent
Chan

(10) Patent No.: US 6,455,318 B1
(45) Date of Patent: Sep. 24, 2002

(54) COLLAGEN IV ADHESION ASSAY FOR INTRAOCULAR LENS MATERIALS

(75) Inventor: Kwan Chan, Fort Worth, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/934,400

(22) Filed: Aug. 21, 2001

Related U.S. Application Data

(60) Division of application No. 09/389,436, filed on Sep. 3, 1999, now abandoned, which is a continuation-in-part of application No. 09/283,601, filed on Apr. 1, 1999, now abandoned.
(60) Provisional application No. 60/081,875, filed on Apr. 15, 1998.

(51) Int. Cl.[7] ............................................. G01N 33/00
(52) U.S. Cl. ..................... 436/86; 435/1.1; 435/1.2; 435/402; 514/2; 623/6.11; 623/6.61
(58) Field of Search .................... 435/1.1, 1.2, 402; 623/6.11, 6.61; 514/2; 436/86

(56) References Cited

U.S. PATENT DOCUMENTS

| | | | |
|---|---|---|---|
| 4,515,794 A | 5/1985 | Emery et al. ................ 514/249 |
| 4,725,276 A | 2/1988 | Bissonette et al. ............. 623/6 |
| 4,846,833 A | 7/1989 | Cumming ...................... 623/6 |
| 4,918,165 A | 4/1990 | Soll et al. ..................... 530/391 |
| 4,950,290 A | 8/1990 | Kamerling ...................... 623/6 |
| 5,002,571 A | 3/1991 | O'Donnell, Jr. et al. ........ 623/6 |
| 5,078,740 A | 1/1992 | Walman ....................... 623/36 |
| 5,290,892 A | 3/1994 | Namdaran et al. .......... 526/259 |
| 5,331,073 A | 7/1994 | Weinschenk, III et al. . 526/264 |
| 5,359,021 A | 10/1994 | Weinschenk, III et al. . 526/264 |
| 5,366,501 A | 11/1994 | Langerman ..................... 623/6 |
| 5,370,687 A | 12/1994 | Poler ............................. 623/6 |
| 5,375,611 A | 12/1994 | Lindqvist et al. ........... 128/898 |
| 5,405,385 A | 4/1995 | Heimke et al. ................. 623/6 |
| 5,549,670 A | 8/1996 | Young et al. ................... 623/6 |
| 5,576,345 A | 11/1996 | Mansson et al. ............ 514/449 |
| 5,593,438 A | 1/1997 | Akhavi et al. ................. 623/6 |
| 5,693,094 A | 12/1997 | Young et al. ................... 623/6 |
| 5,733,276 A | 3/1998 | Belkin ........................... 606/6 |
| 5,925,617 A | 7/1999 | Kiritoshi et al. .............. 514/11 |
| 6,027,531 A | 2/2000 | Tassignon ...................... 623/6 |
| 6,187,042 B1 * | 2/2001 | Sheets, Jr. et al. | |

FOREIGN PATENT DOCUMENTS

| | | |
|---|---|---|
| EP | 0 559 820 B1 | 9/1993 |
| EP | 0 904 747 A2 | 3/1999 |
| EP | 0 916 320 A2 | 5/1999 |
| WO | WO 94/11764 | 5/1994 |
| WO | WO 96/34629 | 11/1996 |
| WO | WO 98/15238 | 4/1998 |
| WO | 99/62435 | 12/1999 |

OTHER PUBLICATIONS

Boulton et al., "Adhesion of IOLs to the Posterior Capsule," *British Journal of Ophthalmology*, vol. 82(5); p. 468 (1998).

Cunanan et al., "An In Vitro Test Method to Study Posterior Capsular Opacification," *Investigative Opthalmology & Visual Science*, vol. 38(4), p. S178 (1997).

Gabriel et al., "In Vitro Adherence of *Pseudomonas aeruginosa* to Four Intraocular Lenses," *J. Cataract Refractive Surg*, vol. 24, pp. 124–129 (1998).

Hollick et al., "Lens Epithelial Cells Regression on the Posterior Capsule: A 2 Year Prospective, Randomised Trial With Three Different IOL Materials," *Investigative Ophthalmology & Visual Science*, vol. 38(4), p. S19 (1997).

Hollick et al., "The Effect of Polymethylmethacrylate, Silicone, and Polyacrylic Intraocular Lenses on Posterior Capsular Opacification 3 Years After Cataract Surgery," *Ophthalmology*, vol. 106(1), pp. 49–55 (1999).

Johnston et al., "In Vitro Protein Adsorption to 2 Intraocular Lens Materials," *J. Cataract Refractive Surgery*, vol. 25; pp. 1109–1115 (1999).

Kanagawa et al., "Presence and Distributino of Fibronectin on the Surface of Implanted Intraocular Lenses in Rabbits," *Graefe's Archive for Clin. & Exp. Ophthalmology*, vol. 228; pp. 398–400 (1990).

Linnola et al., "Acrylate Intraocular Lenses (IOLs) Hinder Posterior Migration of Epithelium; Activity Tested by Corneal Tissue Cultures," *ESCRS Abstracts*, p. 120 (1997).

Linnola et al., "Adhesion of soluble fibronectin, laminin, and collagen type IV to intraocular lens materials," *J. of Cataract & Refractive Surgery*, vol. 25 (11), pp. 1486–1491 (1999).

Linnola et al., "Intraocular Lens Bioactivity Tested Using Rabbit Corneal Tissue Cultures," *J. Cataract & Refractive Surgery*, vol. 25; pp. 1480–1485 (1999).

Linnola, "Sandwich Theory: Bioactivity–based Explanation for Posterior Capsule Opacification," *J. Cataract Refract. Surg.*, vol. 23, pp. 1539–1542 (1997).

Liu et al., "A Study of Human Lens Cell Growth In Vitro," *Inv. Ophthalmology & Vis. Science*, vol. 37(5); pp. 906–914 (1996).

(List continued on next page.)

*Primary Examiner*—Leon B. Lankford, Jr.
(74) *Attorney, Agent, or Firm*—Patrick M. Ryan

(57) ABSTRACT

A method for determining the propensity of an intraocular lens material to prevent posterior capsule opacification is disclosed. The method involves incubating replicate samples of an IOL material with collagen IV, washing off any loosely bound collagen IV. Following the washing step, one sample is counted to determine the amount of collagen IV that remains adhered to the IOL material. A second sample is further processed prior to counting by subjecting it to a desorption step and a further washing step.

17 Claims, 5 Drawing Sheets

OTHER PUBLICATIONS

Mandle, "Acrylic Lenses Cause Less Posterior Capsule Opacification than PMMA, Silicone IOLs," *Ocular Surgery News*, vol. 14(15), p. 23 (1996).

Nagamoto et al., "Effect of Intraocular Lens Design on Migration of Lens Epithelial Cells Onto the Posterior Capsule," *J. Cataract Refract. Surg.*, vol. 23, pp. 866–872 (1997).

Nagata et al., "Adhesiveness of AcrySof to a Collagen Film," *J. Cataract Refract. Surg.*, vol. 24, pp. 367–370 (1998).

Nagata et al., "Optic Sharp Edge or Convexity; Comparison of Effects of Posterior Capsular Opacification," *Jpn J. Ophthal.*, vol. 40, pp. 397–403 (1996).

Nishi et al., Inhibition of Migrating Lens Epithelial Cells By Blocking The Adhesion Molecule Integrin: A Preliminary Report, *J. Cataract Refract. Surg*, vol. 23 (1997).

Nishi et al., "Preventing Posterior Capsule Opacification by Creating a Discontinuous Sharp Bend in the Capsule," *J. Cataract Refract. Surg.*, vol. 25, pp. 521–526 (1999).

Oshika et al., "Adhesion of Lens Capsule to Intraocular Lenses of Polymethylmethacrylate, Silicone and Acrylic Foldable Materials: An Experimental Study," *British Journal of Ophthalmology*, vol. 82, pp. 549–553 (1998).

Oshika et al., "Incision/Phacoemulsification," Symposium on Cataract, IOL and Refractive Surgery, Jun., 1996.

Oshika et al., "Two Year Clinical Study of a Soft Acrylic Intraocular Lens," *J. Cataract Refract. Surg.*, vol. 22, pp. 104–109 (1996).

Pande et al., "High–Resolution Digital Retroillumination Imaging of the Posterior Lens Capsule After Cataract Surgery," *J. Cataract Refract. Surg.*, vol. 23, pp. 1521–1527 (1997).

Pande et al., "Posterior Capsular Opacfication With PMMA, Silicone and Acrysof Intraocular Lenses: A Prospective Randomized Clinical Trial," *Investigative Ophthalmology & Visual Science*, vol. 36(4), p. S397 (1995).

Reich et al., "Intraocular–Lens–Endothelial Interface: Adhesive Force Measurements," *J. of Biomedical Materials Research*, vol. 18, pp. 737–744 (1984).

Saika et al., "Cell Proliferation on the Outer Anterior Capsule Surface After Extracapsular Lens Extraction in Rabbits," *J. Cataract Refractive Surg.* vol. 23, pp. 1528–1531 (1997).

Ursell et al., Anterior Capsule Stability in Eyes With Intraocular Lenses Made of Poly(methylmethacrylate), Silicone, and AcrySof, *J. Cataract Refractive Surg.*, vol. 23, pp. 1532–1538 (1997).

Ursell et al., "Relationship Between Intraocular Lens Biomaterials and Posterior Capsule Opacification," *J. Cataract Refractive Surg.* vol. 24, pp. 352–360 (1998).

Ursell et al., "The In Vivo Movement of Cells on the Surface of Intraocular Lenses in Humans Observed with Sequential Specular Photomicrography," *Investigative Ophthalmology & Visual Science*, vol. 36(4), S795 (1995).

Werner et al., "Endothelial Damage Caused by Uncoated and Fluorocarbon–Coated Poly(methylmethacrylate) Intraocular Lenses,"*J. Cataract Refractive Surgery*, vol. 23, pp. 1013–1019 (1997).

Yang et al., "Membrane Formation and Cellular Response on the Surface of Lenses Implanted in Rabbit Eyes," *J. Cataract Refractive Surg.*, vol. 23, pp. 1265–1270 (1997).

International Standard ISO/FDIS 11979–1:1999(E).

* cited by examiner

COLLAGEN IV ADHESION ASSAY FOR INTRAOCULAR LENS MATERIALS

This application is a divisional application of U.S. patent application Ser. No. 09/389,436, filed Sep. 3, 1999 now abandoned, which is a continuation-in-part application of U.S. patent application Ser. No. 09/283,601, filed Apr. 1, 1999 now abandoned, which claims priority from U.S. Provisional Patent Application No. 60/081,875, filed Apr. 15, 1998.

FIELD OF THE INVENTION

This invention relates to intraocular lenses. In particular, the present invention relates to methods for determining whether intraocular lens materials have a propensity for preventing posterior capsule opacification.

BACKGROUND OF THE INVENTION

Foldable intraocular lens ("IOL") materials can generally be divided into three categories: silicone materials, hydrogel materials, and non-hydrogel acrylic materials. Many materials in each category are known. See, for example, *Foldable Intraocular Lenses*, Ed. Martin et al., Slack Incorporated, Thorofare, N.J. (1993). Biocompatibility varies among different IOL materials within and among each category. Although the distinction between hydrogel and non-hydrogel acrylic materials is sometimes unclear, for purposes of the present application, acrylic materials that absorb 5% (by weight) or less water at 37° C. are considered non-hydrogel acrylic materials.

One measure of biocompatability for an IOL can be the incidence of posterior capsule opacification ("PCO"). A number or factors may be involved in causing and/or controlling PCO. For example, the design and edge sharpness of an IOL may be a factor. See, Nagamoto et al., J. Cataract Refract. Surg., 23:866–872 (1997); and Nagata et al., Jpn. J. Ophthalmol., 40:397–403 (1996). See, also, U.S. Pat. Nos. 5,549,670 and 5,693,094. Another factor appears to be the lens material itself. See, for example, Mandle, "Acrylic lenses cause less posterior capsule opacification than PMMA, silicone IOLs," Ocular Surgery News, Vol. 14. No. 15, p. 23 (1996). See, also, Oshika, et al., "Two Year Clinical Study of a Soft Acrylic Intraocular Lens," J. Cataract. Refract. Surg., 22:104–109 (1996); and Ursell et al., "Relationship Between Intraocular Lens Biomaterials and Posterior Capsule Opacification," J. Cataract Refract. Surg., 24:352–360 (1998).

One method of addressing the PCO problem involves administering a pharmaceutical agent to the capsular bag area at the time of, or immediately after, extracapsular cataract extraction. See, for example, U.S. Pat. No. 5,576,345 (pharmaceutical agent=the cytotoxic agent taxol or an ophthalmically acceptable derivative); U.S. Pat. Nos. 4,515,794; and 5,370,687. Alternatively, the pharmaceutical agent may be tethered to the surface of the IOL material. See, for example, U.S. Pat. No. 4,918,165. The pharmaceutical agents are intended to kill or prevent the growth of proliferating cells that might cause PCO or "secondary cataracts." Yet another method involves the physical destruction or removal of lens epithelial cells. See, Saika et al., J. Cataract Refract. Surg., 23:1528–1531 (1997).

Another method of addressing PCO is the prophylactic laser therapy method disclosed in U.S. Pat. No. 5,733,276. According to this method, the lens capsule is irradiated with laser irradiation to destroy cells which remain in the lens capsule after extraction of a cataract.

Other methods theorized for reducing the risk of PCO involve adhering the posterior capsule to the IOL at the time of implantation, as in U.S. Pat. No. 5,002,571. According to the '571 patent, a non-biological glue or, preferably, a biological glue, such as fibrin, collagen, or mussel glue, is used to adhere the posterior lens capsule to the posterior surface of an IOL. The glue may be applied over the entire posterior surface of the IOL or just as an annulus around the outer perimeter of the posterior surface of the IOL.

In contrast, U.S. Pat. No. 5,375,611 discloses a method of reducing the risk of PCO by preventing the adherence of the posterior capsule to the IOL. According to the '611 patent, the posterior surface of the lens capsule itself is chemically modified at the time of extracapsular cataract extraction. The chemical modification is achieved by depositing a water-insoluble stable or permanent layer of a cell attachment preventing compound onto the posterior surface of the lens capsule. The stable or permanent layer may be a polymer, such as polyethylene glycol, polysaccharides, polyethylenepropylene glycol, and polyvinyl alcohols.

SUMMARY OF THE INVENTION

The present invention relates to a method of determining the propensity of an intraocular lens ("IOL") material to prevent posterior capsule opacification ("PCO"). The method involves incubating replicate samples of an IOL material in a liquid composition comprising collagen IV for a time sufficient to allow at least some of the collagen IV to be adsorbed onto the surface of the IOL material, washing off any loosely bound collagen IV, and then determining for a first sample the amount of collagen IV that remains bound to the IOL material after washing. A second sample is further processed by subjecting it to a collagen IV desorption step and a second washing step. The amount of collagen IV that remains bound to the second sample of IOL material following the desorption and second washing steps is then determined and compared to the amount that remained bound to the first sample. The amount of collagen IV that remains bound after the desorption step can be considered to be specifically or permanently bound, in contrast to any amount of collagen IV that is only non-specifically or transiently bound to the IOL material.

The present invention also relates to IOL materials capable of permanently binding to collagen IV to an extent sufficient to allow an IOL posterior optic surface that contacts the posterior lens capsule to prevent PCO. Without intending to be bound by any theory, it is believed that IOL posterior surfaces that specifically and strongly bind to the lens capsule significantly reduce the risk of or prevent PCO.

DETAILED DESCRIPTION OF THE INVENTION

Figure 1:
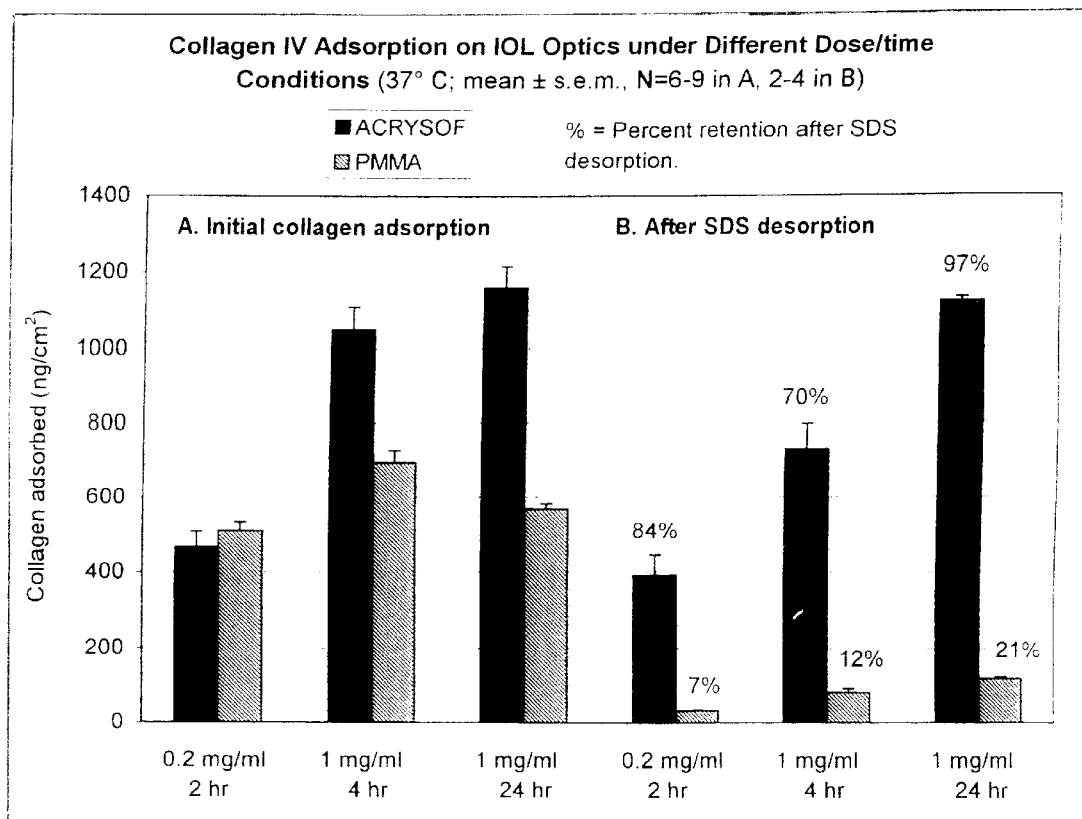
FIG. 1 compares the collagen IV adsorption on ACRYSOF and PMMA materials under different dose/time and washing conditions. Dose refers to the concentration of collagen IV in the liquid composition contacted with the test IOL material. Time refers to the duration of the IOL material's exposure to the liquid composition comprising collagen IV.

According to the present invention, the propensity of an IOL material to prevent PCO is determined by a method comprising the steps of:

a) incubating a first and second replicate samples of the IOL material in a liquid composition comprising collagen IV at approximately human body temperature for a time sufficient to allow at least some of the collagen IV to adhere to the IOL material;

b) washing any loosely bound collagen IV off of the first and second replicate samples with a washing composition that lacks a collagen IV desorption agent;

c) determining the amount of collagen IV that remains adhered to the first replicate sample;

d) incubating the second replicate sample in a solution comprising a collagen IV desorption agent, wherein the solution has an approximately neutral pH and a temperature of about human body temperature; and e) washing the second replicate sample in a composition lacking a collagen IV desorption agent; and f) determining the amount of collagen IV that remains adhered to the second sample and comparing it to the amount of step (c).

The IOL material to be tested according to the method of the present invention is prepared to form samples that can be of almost any size or shape, but are preferably the size and shape of an IOL optic. Two replicate samples of the same IOL material, having approximately identical size and shape, are generally required. (It is possible to use only one sample for the method of the present invention, but using two samples is much more efficient).

As used herein, "collagen IV desorption agent" means an agent selected from the group consisting of (i) hydrophobic agents, such as lipids, and (ii) surfactants.

[Step (a): Collagen IV Adsorption Step]

In the first step of the method of the present invention, each of two replicate samples is incubated in a liquid composition comprising collagen IV at approximately human body temperature for a time sufficient to allow at least some of the collagen IV to adhere to the IOL material.

Human, bovine and rabbit collagen IV, and perhaps other species' collagen IV as well, are commercially available. Human collagen IV is preferred. Collagen IV is usually supplied in the form of a dry powder, but, as in the case of tritium-radiolabelled collagen IV, for example, can also be supplied in the form of a solution comprising acetic acid. If obtained in dry powder form, the collagen IV can be dissolved using a diluted weak acid, such as acetic acid. For example, the collagen IV can be dissolved in a 10 $\mu$M solution of acetic acid in deionized water. The amount of collagen IV contained in the liquid composition comprising collagen IV will generally be about 2 mg/ml or less, and is preferably about 0.2 mg/ml.

The liquid collagen IV composition should be at approximately neutral pH (about pH 7–7.6) and human body temperature (about 35–37° C.). The liquid collagen IV composition is preferably at pH 7.2–7.4. The liquid collagen IV composition is preferably a buffered salt solution, such as Tris-buffered BSS® or a buffered 0.9% NaCl solution, having an osmolarity approximately equal to that of aqueous humor. The amount of the liquid collagen IV composition comprising collagen IV to be used for each IOL material sample should be that amount sufficient to completely submerse the sample in the liquid composition. The samples are preferably isolated in individual vials, such as plastic microfuge tubes of 1.5–2 ml size, rather than combined in a bath.

The IOL material sample should be incubated in the liquid collagen IV composition for time sufficient to allow at least some of the collagen IV to adhere to the surface of the sample. Depending upon the size and shape of the sample, the identity of the IOL material, the concentration of collagen IV in the liquid collagen IV composition and the amount of the liquid collagen IV composition, etc., the incubation time will generally be about 24 hours or less, preferably about 2–4 hours.

[Step (b): Washing Step for Replicate Samples 1 & 2]

After incubating the samples in step (a), the replicate samples are removed from the liquid collagen IV composition and washed extensively using a washing composition comprising a washing agent selected from the group consisting of water, saline and buffered salt solution, in order to remove any loosely bound collagen IV. The washing composition does not contain any collagen IV desorption agent. The washing agent is preferably a buffered salt solution, such as BSS®. The washing is preferably accomplished by soaking the first and second replicate samples in the buffered salt solution for about 30–60 minutes, with the buffered salt solution being replaced with fresh buffered salt solution at about 5–10 minute intervals. This washing step is preferably carried out at a temperature of 20–37° C.

[Step (c): Determining Amount of Collagen IV Adhered to Replicate Sample 1]

After washing in step (b), the amount of collagen IV remaining adhered to the first replicate sample is determined. Suitable methods for determining the amount of collagen IV adhered to the sample include radiolabelling, dye-staining and immunochemical methods. Examples of radiolabelling methods include liquid scintillation counting (e.g., with tritium or $^{14}C$) and gamma isotope counting (e.g., $^{125}I$) methods. If a radiolabelling method is used, the liquid collagen IV composition of step (a) also comprises radiolabelled collagen in an amount of about 2 $\mu$Ci/ml or less, and preferably about 1 $\mu$Ci/ml.

[Step (d): Surfactant Desorption Step]

After washing in step (b), the second replicate sample is incubated in a composition comprising a collagen IV desorption agent, wherein the composition has an approximately neutral pH and a temperature of approximately human body temperature. Collagen IV desorption agents include hydrophobic agents, such as lipids, and surfactants. Preferred collagen IV desorption agents are surfactants. Although not essential, the collagen IV desoption agent can be contained in water, saline, or buffered salt solution. For example, the desoption composition can comprise a surfactant in deionized water buffered with 10 mM phosphate buffer. Suitable surfactants include almost any surfactant; it is not essential that the surfactant be non-ionic, anionic or cationic. Preferred surfactants include sodium dodecyl sulfate and Triton X-100. In general, the amount of the collagen IV desorption agent contained in the desorption composition will be about 4% (w/v) or less, and preferably about 2% (w/v). The incubation time for this desorption step (step (d)) is generally about 60 minutes or less, and preferably about 15–30 minutes.

[Step (e): Washing Step for Replicate Sample 2]

After the second replicate sample has been incubated with a composition comprising a collagen IV desorption agent, the second replicate sample is then washed extensively with a composition lacking a collagen IV desorption agent as described in step (b) above. This washing step removes any residual collagen IV desorption agent and any desorbed collagen IV for the second replicate sample. As in step (b) above, the washing composition may be selected from the group consisting of water, saline and buffered salt solution, but is preferably a buffered salt solution such as BSS®. Again as in step (b), the washing is preferably accomplished by soaking the second sample in buffered salt solution for about 30–60 minutes, with the buffered salt solution being replaced with fresh buffered salt solution at about 5–10 minute intervals. This washing step is preferably carried out at a temperature of 20–37° C.

[Step (f): Determining Amount of Collagen IV Adhered to Replicate Sample 2]

After the second replicate sample has been washed in step (e), the amount of collagen IV remaining adhered to the second replicate sample is determined and compared to the amount of step (c). Suitable methods for determining the amount of collagen IV adhered to the sample include those mentioned above.

The method of the present invention can be used to select IOL materials that are capable of reducing the risk of or preventing PCO. Many IOL materials are known, including silicone, hydrogel and foldable non-hydrogel acrylic hydrophobic IOL materials. According to the present invention, IOL materials are screened for their ability to permanently adhere to collagen IV. IOL materials for which the amount of collagen IV that remains adhered to the material in step (f) is about 30–100% of the amount that remains adhered in step (c) are preferred. Even more preferred are IOL materials for which the amount of collagen IV that remains adhered to the material in step (f) is about 50–100% of the amount that remains adhered in step (c). Most preferred are IOL materials for which the amount of collagen IV that remains adhered to the material in step (f) is about 75–100% of the amount that remains adhered in step (c). The IOL material does not consist essentially of (i) 2-phenylethyl methacrylate and 2-phenylethyl acrylate; (ii) ethyl acrylate, ethyl methacrylate and trifluoroethylmethacrylate; or (iii) 2-phenylethyl acrylate and 2-hydroxyethylmethacrylate. Suitable IOL materials for screening using the method of the present invention include soft acrylic materials, including but not limited to those disclosed in U.S. Pat. Nos. 5,290,892 and 5,331,073, the entire contents of which are hereby incorporated by reference. The IOL materials of the present invention are used to form IOL bodies or are used to coat all or part of an IOL body. Preferably, at least a portion of the posterior surface of the IOL body comprises the materials of the present invention.

Also preferred are IOL materials which are substantially free of glistenings in a physiologic environment and for which the amount of collagen IV that remains adhered to the material in step (f) is about 30–100% of the amount that remains adhered in step (c). Glistenings are the result of condensation of water vapor within the lens. Although glistenings have no detrimental effect on the function or performance of IOLs made from acrylic materials, it is nevertheless cosmetically desirable to minimize or eliminate them. IOL materials are substantially free of glistenings in a physiologic environment if they have an average of no more than approximately 1–2 glistenings per $mm^2$ when evaluated in the test described below. Preferably, the average number of glistenings per $mm^2$ will be much less than 1.

The presence of glistenings is measured by placement of a lens sample into a vial and adding deionized water or a balanced salt solution. The vial is then placed into a water bath preheated to 45° C. Samples are to be maintained in the bath for 24 hours. The sample is then placed either in a 37° C. bath or at room temperature and allowed to equilibrate for 2 hours. The sample is removed from the vial and placed on a microscope slide. Visualization of glistenings is done with light microscopy using a magnification of 50 to 200×.

Preferably, IOL materials are also selected so that they possess the following refractive index, $T_g$, and elongation properties, which make the materials particularly suitable for use in IOLs which are to be inserted through incisions of 5 mm or less.

The IOL material preferably has a refractive index of at least about 1.50 as measured by an Abbe' refractometer at 589 nm (Na light source). IOL optics made from materials having a refractive index lower than 1.50 are necessarily thicker than optics of the same power which are made from materials having a higher refractive index. As such, IOL optics made from materials having a refractive index lower than about 1.50 generally require relatively larger incisions for IOL implantation.

The glass-transition temperature ("Tg") of the IOL material, which affects the material's folding and unfolding characteristics, is preferably between about −20 to +25° C., and more preferably between about −5 and +16° C. Tg is measured by differential scanning calorimetry at 10° C./min., and is determined at the midpoint of the transition of the heat flux curve.

The IOL material should also have an elongation of at least about 150%, preferably at least 200%, and most preferably about 300–600%. This property indicates that an IOL optic made of the material generally will not crack, tear or split when folded. Elongation of polymer samples is determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on samples at ambient conditions using an Instron Material Tester (Model No. 4442 or equivalent) with a 50 Netwon load cell. The grip distance is set at 14 mm and a crosshead speed is set at 500 mm/minute and the sample is pulled until failure. The elongation (strain) is reported as a fraction of the displacement at failure to the original grip distance.

The IOL bodies formed of the materials of the present invention or formed of other materials and coated in whole or in part with the materials of the present invention are preferably designed so that at least one of the optic's anterior and posterior surfaces forms a corner where it meets the optic's edge surface such that, at 150×magnification (of a cross-sectional view), the cornet (i) is a sharp corner having an angle from 70–140°, more preferably 80–130°, and most preferably 90–120°, or (ii) is a round corner that has an arc that subtends an angle of 90° or less to the center of a circle having a radius ≦0.025 mm. As used herein, "optic" and "body" are used interchangeably and both mean the central part of the IOL incorporating the image-forming component of the IOL (see the definition of "body" in ISO/FDIS 11979-1:1999 (E)).

The invention will be further illustrated by the following examples, which are intended to be illustrative, but not limiting.

EXAMPLES

1. PMMA (polymethylmethacrylate); ACRYSOF (65 wt. % 2-phenylethyl acrylate; 30 wt. % 2-phenylethyl methacrylate; 3.2 wt. % 1,4-butanediol diacrylate; and 1.8 wt. % 2-(3'-methallyl-2'-hydroxy-5'-methyl phenyl) benzotriazole) with (P) and without (NP) Argon plasma gas treatment according to U.S. Pat. No. 5,603,774; ACRYSOF II (80 wt. % 2-phenylethyl acrylate; 15 wt.% 2-hydroxyethylmethacrylate; 3.2 wt. % 1,4-butanediol diacrylate; and 1.8 wt. % 2-(3'-methallyl-2'-hydroxy-5'-methyl phenyl) benzotriazole) with (P) Argon plasma gas treatment according to U.S. Pat. No. 5,603,774; and silicone (SI-30 from Allergan Medical Optic) were analyzed according to the method of the present invention.

The dose (concentration of collagen IV in the liquid composition of step (a)) was varied from 0.2 mg/ml–1 mg/ml. The incubation time for step (a) was also varied from 2–24 hours. The liquid composition of step (a), which was 37° C. and had a pH of 7.4, comprised Tris-buffered BSS® containing human collagen IV (dissolved with the help of acetic acid) and radiolabelled (tritium) human collagen IV in an amount of about 1 $\mu$Ci/ml. The washing of step (b) was accomplished by incubating the samples in 37° C. BSS® for >40 minutes, including replacing the BSS® with fresh BSS® every 5–10 minutes. The desorption step (d) was accomplished by incubating the samples for 30 minutes in a 37° C., pH 7.4 composition comprising 2% (w/v) of sodium dodecyl sulfate. The surfactant composition was buffered with 10 mM phosphate buffer. After the second replicate samples were removed from the surfactant composition, they were washed as in step (b) above.

Figure 2:
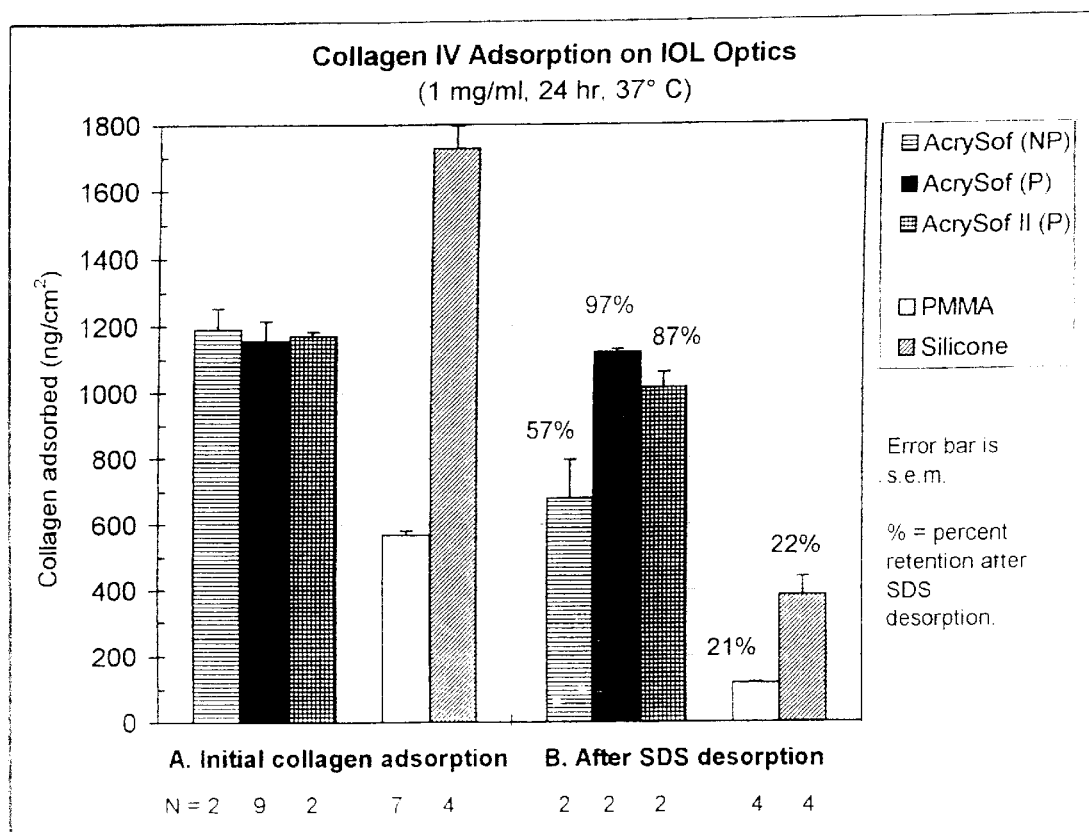
FIG. 2 compares the amount of collagen IV remaining adsorbed on various IOL materials following the initial collagen IV adsorption and washing steps to the amount remaining after the surfactant (sodium dodecyl sulfate, "SDS") desorption and second washing steps.

The amount of collagen IV adhered to the samples was determined using a scintillation solution and counted in a β-counter. The data is expressed as amount of collagen IV adsorbed per surface area (ng/cm$^2$). Each run consisted of two replicate samples of the IOL material in the shape of an IOL optic. The first replicate sample was subjected to step (a) and the washing step of step (b) and then counted using the β-counter (step (c)). The second replicate sample was subjected to step (a), the washing step of step (b), the desorption step of step (d), the washing step of step (b) again (i.e., step (e)), and then counted using the β-counter (step (f)). The percent retention of collagen IV after SDS desorption is determined by comparing (step (f)) the amount of collagen IV adhered to the second replicate sample to that adhered to the first replicate sample. The results are shown in FIGS. 1 and 2.

2. The edge profile of an IOL body is measured by cutting a cross-sectional slice (0.5 mm thick) of the IOL body along the mid-line. The slice is mounted on its side on a microscope slide to produce a cross-sectional view of the optic under microscope at 150×magnification. A digital image of the edge profile is recorded by camera and later reproduced on a computer monitor. In general, the corner of the body edge formed with the anterior or posterior body surface is either sharp or round. A sharp corner is defined by the angle (in degrees) between tangents to the body surface (anterior or posterior) and edge surface at the point of their intersection. This angle is measured by placing a pre-calibrated image of a protractor on the corner. A round corner is defined by the arc forming the corner. This arc is measured by fitting different circles of calibrated radius to coincide with the arc. The angle (in degrees) subtended by the arc of best fit at the center of the fitting circle of known radius is measured by protractor.

Figure 3:
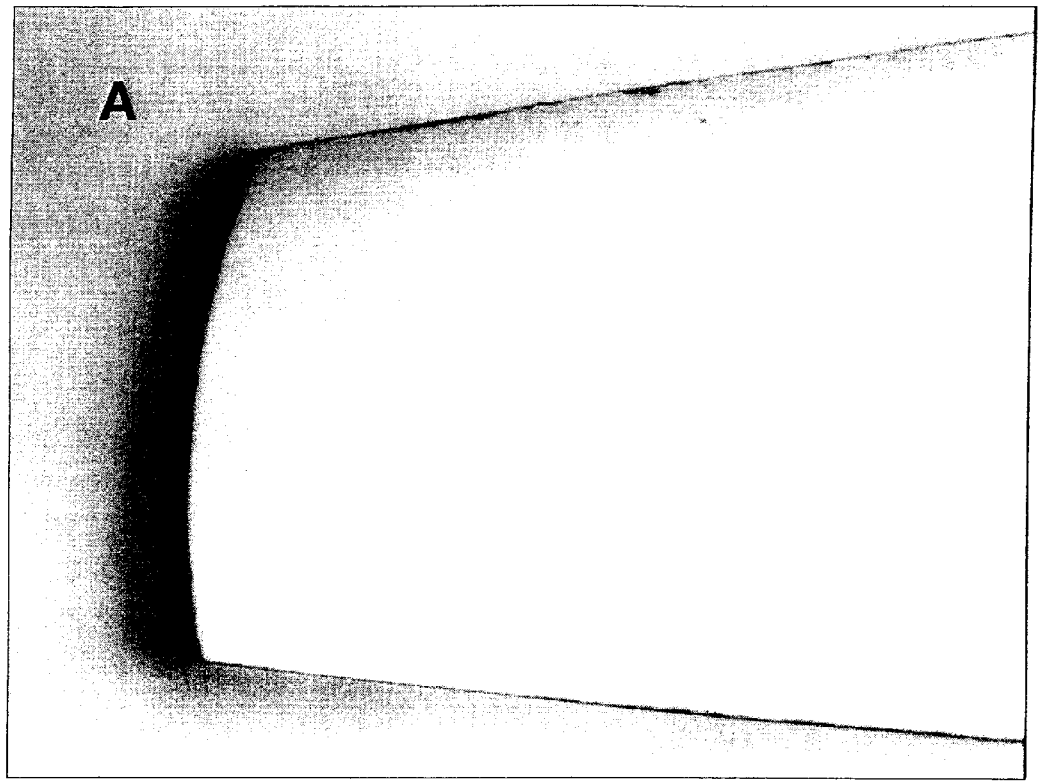
FIG. 3A shows an edge profile of an ACRYSOF® non-hydrogel acrylic IOL (model MA60BM) optic at a magnification of 150×.
FIG. 3B shows an edge profile of an ACRYSOF® non-hydrogel acrylic IOL (model MA60BM) optic at a magnification of 150× with anterior side (up) and posterior side (down) sharp corner angles identified.
Figure 3:
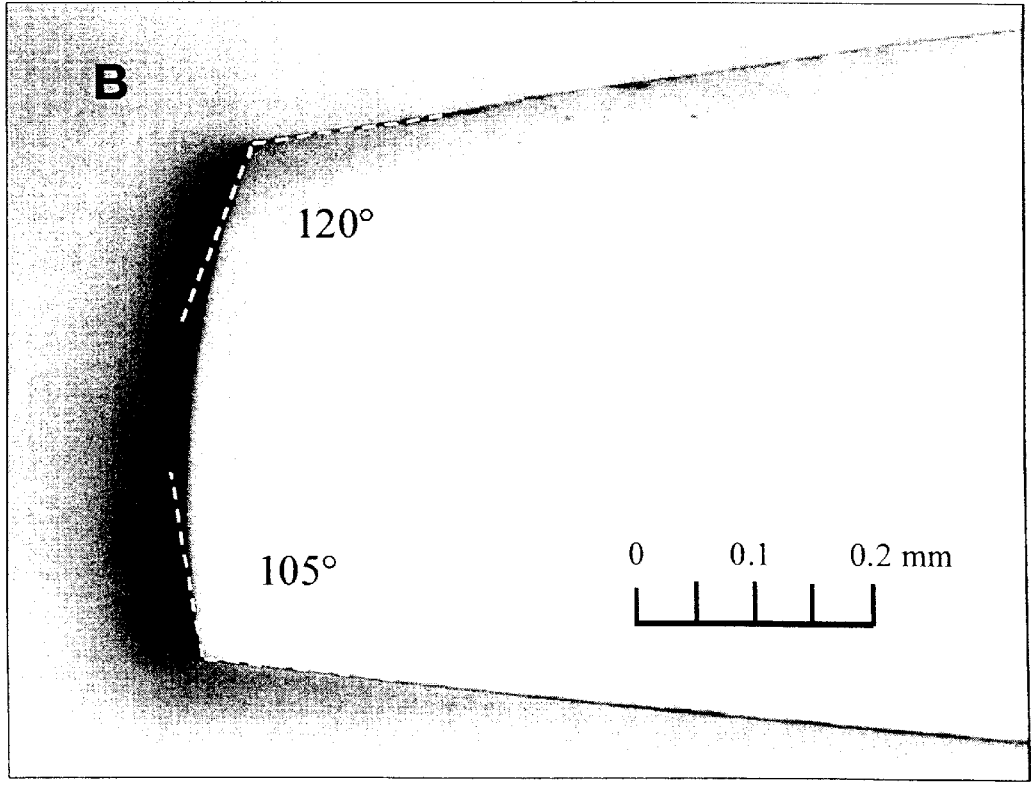

FIG. 3 shows edge profile of ACRYSOF IOL model MA60BM, with the anterior surface of optic facing up in A. In B, the angles of the sharp corners are indicated. The angle between tangents to the optic surface (anterior or posterior) and edge surface at the point of their intersection is measured in degrees.

Figure 4:
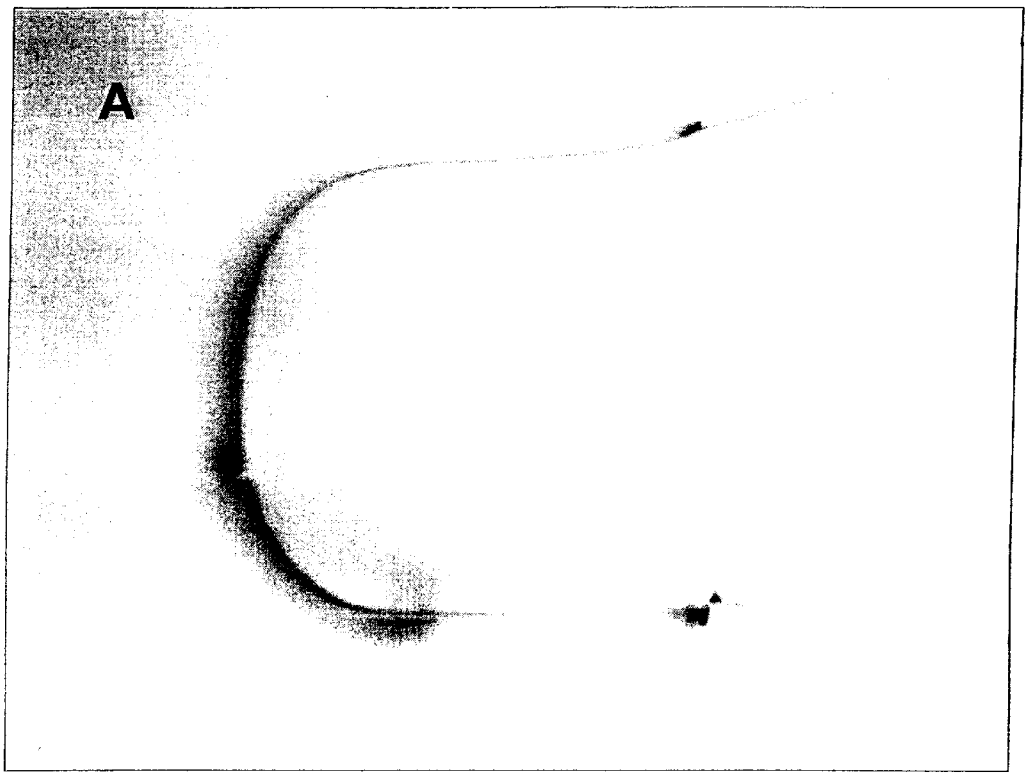
FIG. 4A shows an edge profile of a silicone IOL (model SI30NB) optic at a magnification of 150×.
FIG. 4B shows an edge profile of a silicone IOL (model SI30NB) optic at a magnification of 150× with anterior and posterior side round corners identified.
Figure 4:
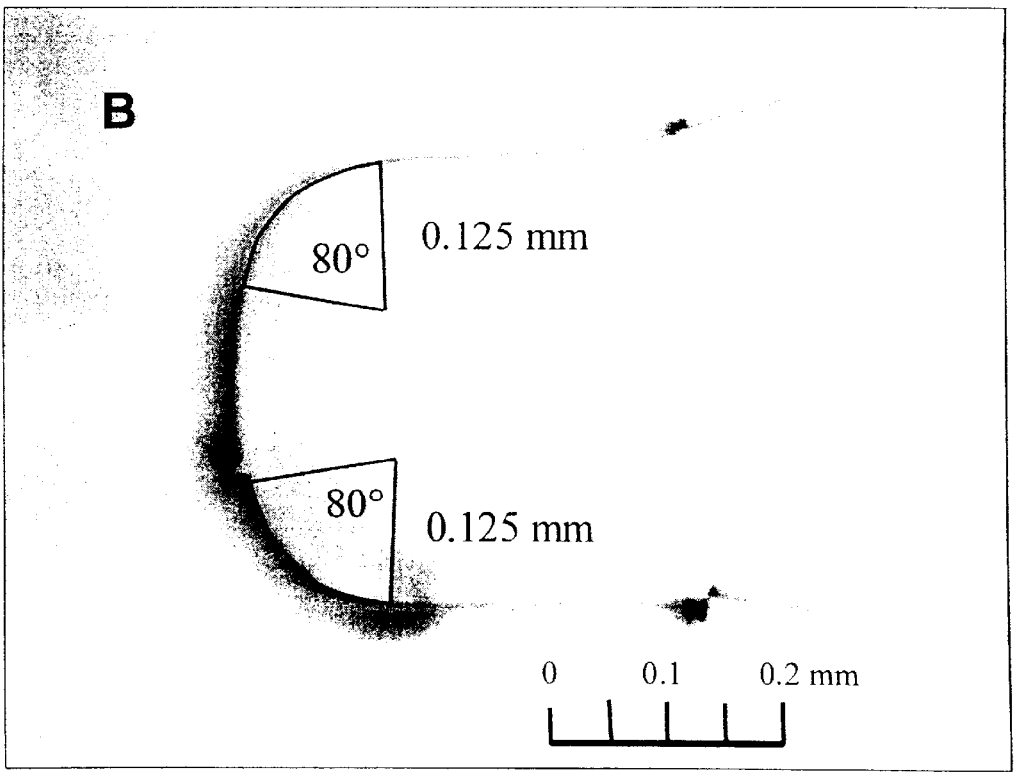

FIG. 4 shows edge profile of silicone IOL model SI30NB in A, and in B the manner with which the arc forming the round corners are measured. The arc of best fit is measured by the angle that the arc subtends at the center of the fitting circle of calibrated radius, in this case 0.125 mm.

Figure 5:
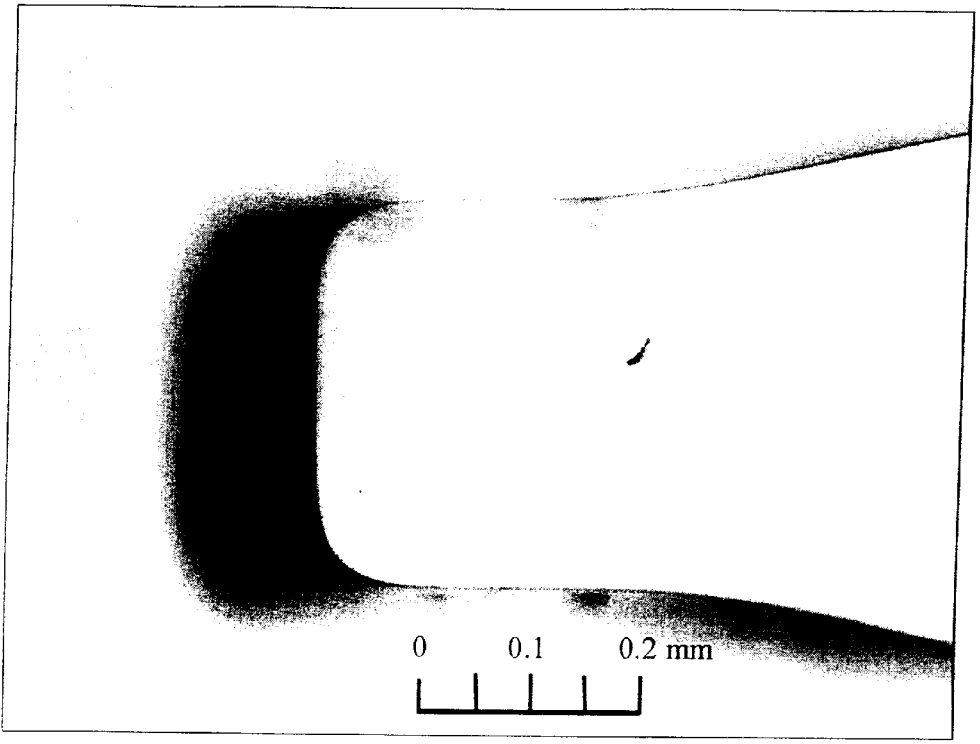
FIG. 5 shows an edge profile of a SENSAR® non-hydrogel acrylic IOL (model AR40) optic at a magnification of 150×.
Figure 6:
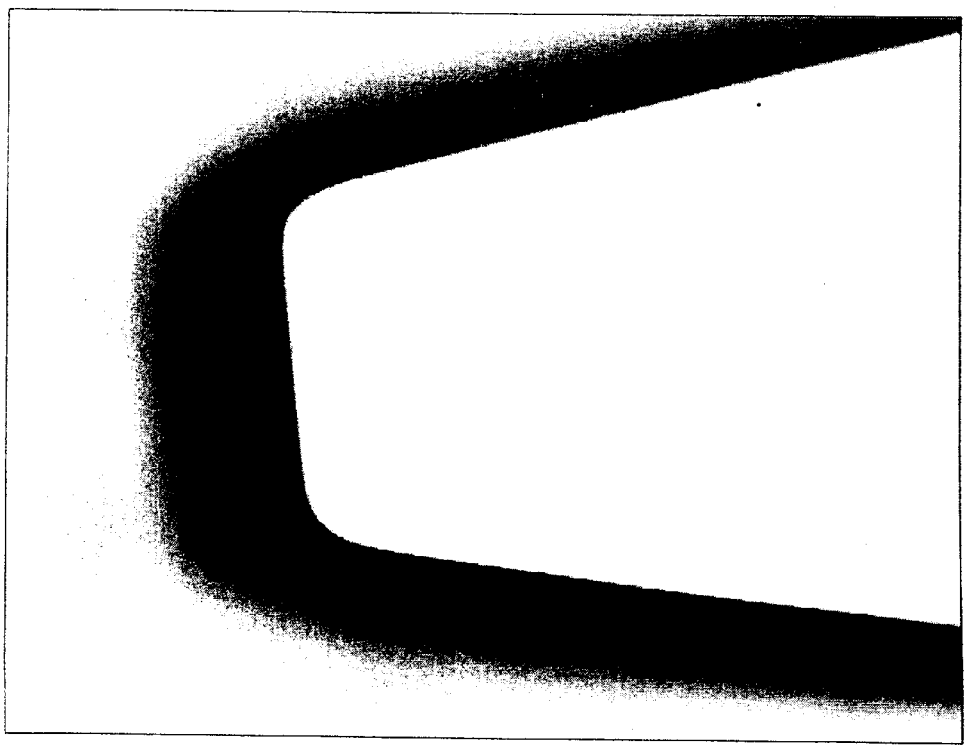
FIG. 6 shows an edge profile of a HYDROVIEW® hydrogel IOL (model H60M) optic at a magnification of 150×.

FIGS. 5 and 6 show the edge profiles of acrylic SENSAR® IOL model AR40 and hydrogel HYDROVIEW® IOL model H60M, respectively. Both IOLs have round corners on the optic edge. The arcs forming the round corners of AR40 are 80° with radius 0.05–0.075 mm, and of H60M are 60–80° with radius of 0.05 mm.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

I claim:

1. A method of determining the amount of collagen IV that permanently binds to an intraocular lens material comprising the steps of:
    a) incubating a first and second replicate samples of the IOL material in a liquid composition comprising collagen IV at approximately human body temperature for a time sufficient to allow at least some of the collagen IV to adhere to the IOL material;
    b) washing any loosely bound collagen IV off of the first and second replicate samples with a washing composition that lacks a collagen IV desorption agent
    c) determining the amount of collagen IV that remains adhered to the first replicate sample;
    d) incubating the second replicate sample in a solution comprising a collagen IV desorption agent, wherein the solution has an approximately neutral pH and a temperature of about human body temperature; and
    e) washing the second replicate sample in a composition lacking a collagen IV desorption agent; and
    f) determining the amount of collagen IV that remains adhered to the second replicate sample and comparing it to the amount of step (c).

2. The method of claim 1 wherein the collagen IV is selected from the group consisting of: human collagen IV; bovine collagen IV; and rabbit collagen IV.

3. The method of claim 1 wherein the solution comprising collagen IV of step (a) is a buffered salt solution having an approximately neutral pH and containing about 2 mg/ml or less of collagen IV.

4. The method of claim 3 wherein the solution comprising collagen IV of step (a) contains about 0.2 mg/ml of collagen IV.

5. The method of claim 1 wherein the collagen IV desorption agent in step (d) is a surfactant selected from the group consisting of sodium dodecyl sulfate and Triton X-100.

6. The method of claim 1 wherein the amount of the collagen IV desorption agent in the composition of step (d) is about 4% (w/v) or less.

7. The method of claim 6 wherein the amount of the collagen IV desorption agent in the composition of step (d) is about 2% (w/v).

8. The method of claim 1 wherein the composition comprising collagen IV of step (a) further comprises radio-labelled collagen IV in an amount of about 2 $\mu$Ci/ml or less and the method of determining the amount of collagen IV in steps (c) and (f) is selected from the group consisting of liquid scintillation counting methods and gamma isotope counting methods.

9. The method of claim 8 wherein the amount of radio-labelled collagen IV is about 1 $\mu$Ci/ml.

10. The method of claim 1 wherein the method of determining the amount of collagen IV in steps (c) and (f) is selected from the group consisting of dye-staining methods and immunochemical methods.

11. The method of claim 1 wherein the incubation time in step (a) is about 24 hours or less.

12. The method of claim 11 wherein the incubation time in step (a) is about 2–4 hours.

13. The method of claim 1 wherein the second replicate sample is incubated in step (d) for about 60 minutes or less.

14. The method of claim 13 wherein the second replicate sample is incubated in step (d) for about 15–30 minutes.

15. The method of claim 1 wherein the washing composition lacking a collagen IV desorption agent in step (b) and step (e) is selected from the group consisting of deionized water; saline; and buffered salt solution.

16. The method of claim 15 wherein the washing composition is buffered salt solution and the washing is accomplished by incubating the first and second replicate samples in buffered salt solution for about 30–60 minutes, and wherein the buffered salt solution is replaced at about 5–10 minute intervals.

17. The method of claim 1 wherein approximately neutral pH is about 7.2–7.4.

\* \* \* \* \*